United States Patent
Chen

Patent Number: 5,164,389
Date of Patent: Nov. 17, 1992

[54] ANTHELMINTIC BIOCONVERSION PRODUCTS

[75] Inventor: Shieh-Shung T. Chen, Morganville, N.J.

[73] Assignee: Merck & Co., Inc., Rahway, N.J.

[21] Appl. No.: 757,434

[22] Filed: Sep. 10, 1991

Related U.S. Application Data

[63] Continuation-in-part of Ser. No. 602,827, Oct. 24, 1990, abandoned, which is a continuation of Ser. No. 330,522, Mar. 30, 1989, abandoned.

[51] Int. Cl.$^5$ .................. C07D 491/22; A61K 31/495
[52] U.S. Cl. ..................................... 514/250; 435/119; 544/350
[58] Field of Search .......................... 544/230; 514/250

[56] References Cited

PUBLICATIONS

Blizzard, Chem Abs 111, 7655m (1989).
Yamazaki et al Tetrahedron Letters 22 135-136 (1981).
Blizzard, J. Org. Chem. 54, 2657 (1989).

Primary Examiner—Mark L. Berch
Attorney, Agent, or Firm—David L. Rose; Joseph F. DiPrima

[57] ABSTRACT

There are disclosed new compound with significant antiparasitic activity which are prepared by fermenting the compounds paraherquamide or dihydroparaherquamide in a novel microorganism identified as Cunninghamella blakesleeana MF-4415. The compounds are best realized in the following structural formulae:

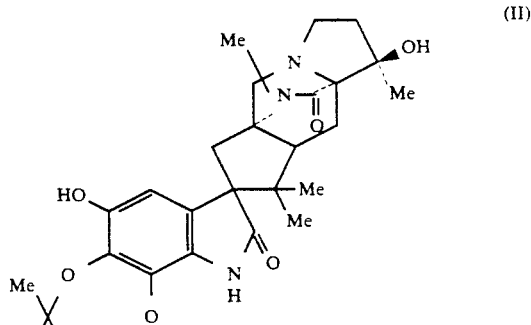

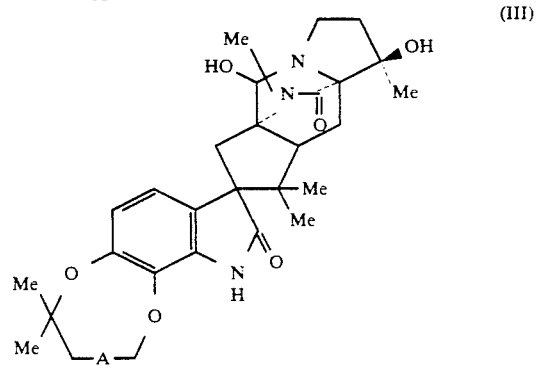

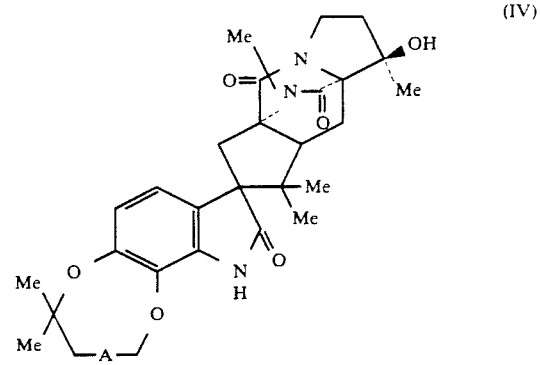

wherein A is either a single or a double bond.

The paraherquamide compound is modified by the microorganism by ring hydroxylation or ketonization. The compounds are significant antiparasitic and anthelmintic agents and compositions for that use are also disclosed.

7 Claims, No Drawings

ANTHELMINTIC BIOCONVERSION PRODUCTS

CROSS REFERENCE TO RELATED APPLICATIONS

This application is a continuation-in-part of copending application Ser. No. 07/602,827 filed Oct. 24, 1990 now abanadoned which in turn is a continuation of my application Ser. No. 07/330,522 filed Mar. 30, 1989, now abandoned.

BACKGROUND OF THE INVENTION

In Yamazaki et al *Tetrahedron Letters* 22 135-136 (1981), there is a disclosed paraherquamide which is isolated as a fungal metabolite. No uses for paraherquamide are disclosed in Yamazaki et al. Also disclosed is the synthetic derivative dihydroparaherquamide produced by the catalytic reduction of paraherquamide. Paraherquamide and dihydroparaherquamide are best described in the following structural formula:

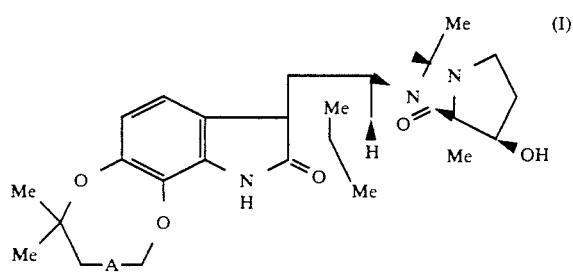

(I)

SUMMARY OF THE INVENTION

The instant invention is concerned with the preparation of novel compounds which are prepared by the bioconversion of the known compound paraherquamide and dihydroparaherquamide in a known microorganism, *Cunninghamella blakesleeana* MF-4415. Thus, it is an object of this invention to describe such novel compounds. It is a further object of this invention to describe the process used to prepare such novel compounds. It is a still further object to describe the novel microorganism used to prepare such compounds. Another object is to describe the use of such compounds as anthelmintic and parasiticidal agents. Additional objects will become apparent from a reading of the following description.

DESCRIPTION OF THE INVENTION

The compounds of the instant invention are best realized in the following structural formulae:

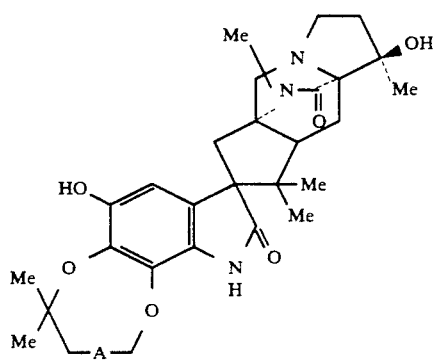

(II)

-continued

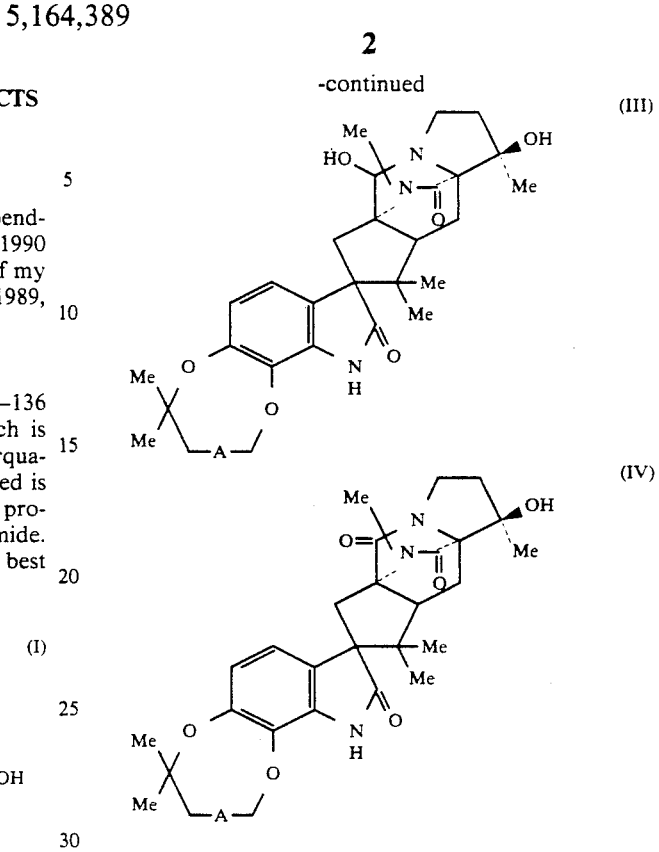

(III)

(IV)

wherein A is either a single or a double bond.

In accordance with this invention, novel substances are described which are prepared by growing under controlled conditions a strain of microorganism identified as *Cunninghamella blakesleeana* MF-4415, ATCC 8688a and including a quantity of paraherquamide or dihyrdoparaherquamide in the fermentation broth. This microorganism is identified in the Merck Culture Collection as MF-4415 and is publicly available from the American Type Culture Collection at 12301 Parklawn Drive, Rockville, MD 20852 under the accession number ATCC 8688a. This same strain has been redeposited at the American Type Culture collection under the accession number ATCC 20926.

The instant compounds are produced during the aerobic fermentation of suitable aqueous nutrient media under conditions described hereinafter, with a strain of *Cunninghamella blakesleeana* MF-4415 ATCC 8688a, 20926. Aqueous media such as those used for the production of many antibiotic substances are suitable for use in the process for the production of these compounds.

Such nutrient media contain sources of carbon and nitrogen assimilable by the microorganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, carbohydrates such as sugars, for example dextrose, sucrose, maltose, lactose, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount of carbohydrate between 1 and 10 g/l in the medium is satisfactory. These carbon sources can be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, distillers solubles, cottonseed meal, meat extract and the like, are readily assimilable by *Cunnighamella blakesleeana* MF-4415, ATCC 8688a, 20926 in the production of the instant compounds. The various sources of nitrogen can be used alone or in combination in amounts ranging from 1 to 5 g/l in the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, and the like.

It should be noted that the media described hereinbelow and in the Examples are merely illustrative of the wide variety of media, which may be employed, and are not intended to be limitative.

The following are Examples of media suitable for growing strains of *Cunnighamella blakesleeana*, MF-4415 ATCC 8688a, 20926:

| Composition of Media | |
|---|---|
| Medium A | |
| Dextrose | 20 g. |
| Peptone | 5 g. |
| Meat Extract | 5 g. |
| Primary Yeast | 3 g. |
| NaCl | 5 g. |
| $CaCO_3$ (after pH adjustment) | 3 g. |
| Distilled Water | 1000 ml. |
| pH 7.0 | |
| Medium B | |
| Tomato Paste | 20 g. |
| Modified Starch (CPC) | 20 g. |
| Primary Yeast | 10 g. |
| $CoCl_2 6H_2O$ | 0.005 g. |
| Distilled Water | 1000 ml. |
| pH 7.2-7.4 | |
| Medium C (Slant Medium) | |
| Dextrose | 10.0 g. |
| Bacto Asparagine | 0.5 g. |
| $K_2HPO_4$ | 0.5 g. |
| Bacto Agar | 15.0 g. |
| Distilled Water | 1000 ml. |
| pH 7.0 | |
| Medium D (Seed Medium) | |
| Soluble Starch | 10.0 g. |
| Ardamine pH | 5.0 g. |
| NZ Amine E | 5.0 g. |
| Beef Extract | 3.0 g. |
| $MgSO_4 7H_2O$ | 0.5 g. |
| Cerelose | 1.0 g. |
| $Na_2HPO_4$ | 0.190 g. |
| $KH_2PO_4$ | 0.182 g. |
| $CaCO_3$ | 0.5 g. |
| Distilled Water | 1000 ml. |
| pH 7.0-7.2 | |
| Medium E | |
| Tomato Paste | 40.0 g. |
| Oat Flour | 10.0 g. |
| Cerelose | 10.0 g. |
| Corn Steep Liquor | 5.0 g. |
| Trace Element Mix | 10.0 ml. |
| Distilled Water | 1000 ml. |
| pH 6.8 | |
| Trace Element Mix I | 1000 ml. |
| $FeSO_4.7H_2O$ | 1000 mg. |
| $MnSO_4.4H_2O$ | 1000 mg. |
| $CuCl_2.2H_2O$ | 25.0 g. |
| $CaCl_2.2H_2O$ | 100.0 mg. |
| $H_2BO_3$ | 56.0 mg. |
| $(NH_4)_2MoO_4.4H_2O$ | 10.0 mg. |
| $ZnSO_4.7H_2O$ | 200.0 mg. |
| Distilled Water | 1000 ml. |
| Medium F | |
| CPC Industrial Starch Modified (Available from CPC Corp.) | 40.0 g. |
| Distiller's Solubles | 7.0 g. |
| Autolyzed Yeast (Ardamine pH available from Yeast Products Inc.) | 5.0 g. |
| $CoCl_2.6H_2O$ | 50.0 mg. |
| Distilled Water | 1000 ml. |
| pH 7.3 | |

The fermentation employing *Cunninghamella blakesleeana*, MF-4415 ATCC 8688 a, 20926 can be conducted at temperatures ranging from about 20° C. to about 40° C. For optimum results, it is most convenient to conduct these fermentations at a temperature in the range of from about 24° C. to about 30° C. Temperatures of about 27°-28° C. are most preferred. The pH of the nutrient medium suitable for producing the instant compounds can vary from about 5.0 to 8.5 with a preferred range of from about 6.0 to 7.5.

The paraherquamide or dihydroparaherquamide is added to the fermentation of *Cunninghamella blakesleeana* MF-4415 ATCC 8688 a, 20926 in quantities of from 0.1 to 1.0 g per liter of fermentation medium. It is preferred to use from 0.1 to 0.5 g per liter. The paraquamide or dihydroparaherquamide may be added at any time during the fermentation cycle. The compounds may be added to the medium ingredients before the culture is added and the fermentation begins or they may be added during the course of the fermentation. In order that the cultures have sufficient time to effect the biotransformation, it is preferred that the paraherquamide compounds be added to the fermentation before 50% of the cycle is completed, preferably before 25% of the cycle is completed.

Small scale fermentations are conveniently carried out by placing suitable quantities of nutrient medium in a flask employing known sterile techniques, inoculating the flask with either spores or vegetative cellular growth of *Cunninghamella blakesleeana* MF-4415, ATCC 8688 a, 20926 loosely stoppering the flask with cotton and permitting the fermentation to proceed in a constant room temperature of about 28° C. on a rotary shaker at from 95 to 300 rpm for about 2 to 10 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Cunninghamella blakesleeana* MF-4415 ATCC 8688a, 20926. The fermentation is allowed to continue for from 1 to 8 days while agitating and/or aerating the nutrient medium at a temperature in the range of from about 24° to 37° C. The degree of aeration is dependent upon several factors such as the size of the fermentor, agitation speed, and the like. Generally the larger scale fermentations are agitated at about 95 to 300 rpm and about 50 to 500 liters per minute (CFM) of air.

The separation of the novel compound from the whole fermentation broth and the recovery of said compounds is carried out by solvent extraction and application of chromatographic fractionations with various chromatographic techniques and solvent systems.

The instant compounds have slight solubility in water, but are soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antiparasitic activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the nonpolar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative thin layer chromatography, high pressure liquid chromatography and the like, with silica gel, aluminum oxide, ion exchange resins, dextran gels and the like, as the chromatographic medium, with various solvents and combinations of solvents as the eluent. Thin layer, high pressure, liquid and preparative layer chromatography may be employed to detect the presence of, and to isolate the instant compounds. The use of the foregoing techniques as well as others known to those skilled in the art, will afford purified compositions containing the instant compounds. The presence of the desired compounds is determined by analyzing the various chromatographic fractions for biological activity of physico-chemical characteristics. The structures of the instant compounds have been determined by detailed analysis of the various spectral characteristics of the compounds, in particular their nuclear magnetic resonance, mass, ultraviolet and infrared spectra.

The novel compounds of this invention have significant parasiticidal activity as anthelmintics, insecticides and acaricides, in human and animal health and in agriculture.

PREPARATION OF STARTING MATERIALS

Paraherquaride is isolated as a fungal metabolite of *Penicillium paraherquei* using standard fermentation and isolation techniques. The analytical and structural characteristics of paraherquamide are described in detail in Yamazaki et al *Tetrahedron Letters* 22 135-136 (1981).

Dihydroparaherquamide is prepared from paraherquamide by catalytic hydrogenation over palladium on a carbon support. The analytical characteristics of dihydroparaherquamide are also given in Yamazaki et al.

A strain of *Penicillium charlesii* is identified in the culture collection of Merck & Co., as MF 5123 and has been deposited at the American Type Culture Collection under the accession number ATCC 20841. The morphological and cultural characteristics of MF 5123 are as follows:

Morphology of MF 5123

Conidiophores are simple or variously branched with each branch bearing a monoverticillate penicillus and conidial chains forming a long narrow compact column. Conidiophore walls are smooth or nearly so. Conidia are mostly globose, $1.8\mu$ to $2.4\mu$, slightly roughened.

Cultural characteristics of MF 5123

Czapek Dox agar

Colonies are white, velvety and raised, becoming grey-green with cream colored areas. The reverse side is yellowish-brown and cream. As culture ages, aerial growth becomes grayish brown to brown and a tan soluble pigment diffuses into medium.

Potato dextrose agar

Colonies are white becoming grey-green, flat, granular. Reverse side is greenish-brown.

Sabouraud Maltose

Colonies are white becoming brownish green with vectors of yellowish-tan, raised, velvety. Reverse side is dark brown. A brown soluble pigment diffuses into agar.

Yeast-extract Malt-extract agar

Colonies are white becoming gray-green with yellowish areas, raised, velvety. Reverse side is dark brown edged with tan.

Corn agar

Colonies are white becoming gray-green, flat, granular. Reverse side is yellowish. As culture ages, it becomes brown with greenish tones.

A comparison with culture descriptions in *A Manual of the Penicillia* by K. B. Raper and C. Thom and with known cultures show this culture to be a new strain of the known species *Penicillium charlesii*.

A sample of MF 5123, *Penicillium charlesii* has been deposited in the permanent culture collection of the American Type Culture Collection at 12301 Parklawn Drive, Rockville, Md. 20852 and has been assigned the accession number ATCC 20841.

The above description is illustrative of a strain of *Penicillium charlesii* MF 5123 which can be employed in the production of the instant starting materials. However, the present invention also embraces mutants of the above described microorganism. For example, those mutants which are obtained by natural selection or those produced by mutating agents including ionizing radiation such as ultraviolet irradiation, or chemical mutagens such as nitrosoguanidine or the like treatments are also included within the ambit of this invention.

Paraherquamide may be prepared during the aerobic fermentation of a producing strain of *Penicillium charlesii* MF 5123 in either an agitated aqueous medium or in a static solid medium.

Where the nutrient medium is an aqueous medium, suitable media such as those used for the production of many antibiotic substances are suitable for use in this process for the production of paraherquamide.

Such nutrient media contain sources of carbon and nitrogen assimilable by the microrganism and generally low levels of inorganic salts. In addition, the fermentation media may contain traces of metals necessary for the growth of the microorganisms, and production of the desired compound. These are usually present in sufficient concentrations in the complex sources of carbon and nitrogen, which may be used as nutrient sources, but can, of course, be added separately to the medium if desired.

In general, ingredients such as sugars, for example dextrose, sucrose, maltose, lactose, glycerol, corn, millet, wheat, dextran, cerelose, corn meal, oat flour, and the like, and starches are suitable sources of assimilable carbon in the nutrient media. The exact quantity of the carbon source which is utilized in the medium will depend, in part, upon the other ingredients in the medium, but it is usually found that an amount between 0.5 and 90% by weight of the medium is satisfactory. These carbon sources may be used individually or several such carbon sources may be combined in the same medium.

Various nitrogen sources such as yeast hydrolysates, yeast autolysates, yeast cells, tomato paste, corn meal, oat flour, soybean meal, casein hydrolysates, yeast extracts, corn steep liquors, corn, millet, wheat, distillers solubles, cottonseed meal, meat extract and the like, are readily assimilable by *Penicillium charlesii* MF 5123 in the production of the instant compound. The various sources of nitrogen can be used alone or in combination in amounts ranging from 0.2 to 95% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, cadmium, zinc, copper, and the like.

It should be noted that the media described hereinbelow and in the Examples are merely illustrative of the wide variety of media, which may be employed, and are not intended to be limitative.

The following are Examples of media suitable for growing strains of *Penicillium charlesii* MF 5123.

| Medium G | |
|---|---|
| Dextrose | 1.0 g. |
| Soluble starch | 10.0 g. |
| Beef extract | 3.0 g. |
| Yeast autolysate (As ardamine pH available from Yeast Products, Inc., Clifton, N.J.) | 5.0 g. |
| NZ Amine-E (casein hydrolysate-available from Humko-Sheffield-Memphis, Tenn.) | 5.0 g. |
| $MgSO_4.7H_2O$ | 0.05 g. |
| Phosphate Buffer | 2.0 ml |
| $CaCO_3$ | 0.5 g. |
| Distilled water | 1000 ml. |
| pH 7.0–7.2 | |
| Phosphate Buffer | |
| $KH_2PO_4$ | 91.0 g |
| $Na_2HPO_4$ | 95.0 g |
| Distilled water | 1000 ml |
| pH 7.0 | |
| Medium H | |
| Tomato paste | 20.0 g. |
| Primary yeast | 10.0 g. |
| Dextrin (CPC starch) | 20.0 g. |
| $CoCl_2.6H_2O$ | 0.005 g. |
| Distilled water | 1000 ml |
| pH 7.2–7.4 | |
| Medium I | |
| Corn meal | 20.0 g. |
| Distillers solubles | 10.0 g. |
| Soybean meal | 15.0 g. |
| Sodium citrate | 4.0 g. |
| $CaCl_2.2H_2O$ | 0.5 g. |
| $MgSO_4.7H_2O$ | 0.1 g. |
| $CoCl_2.6H_2O$ | 0.01 g. |
| $FeSO_4.2H_2O$ | 0.01 g. |
| Polyglycol P2000 (Polypropylene glycol mw 2000) | 2.5 mg. |
| Distilled water | 1000 ml. |
| pH 6.5 | |
| Medium J | |
| Lactose | 20.0 g. |
| Distillers solubles | 15.0 g. |
| Autolyzed yeast (Ardamine pH) | 5.0 g. |
| Distilled water q.s. to | 1000 ml |
| pH 7.0 | |
| Medium K | |
| Tomato paste | 40.0 g. |
| Oat Flour | 10.0 g. |
| Distilled water | 1000 ml |
| pH 7.0 | |
| Medium L | |
| Corn Steep Liquor | 15.0 g. |
| $(NH_4)_2SO_4$ | 4.0 g. |
| $CaCO_3$ | 6.0 g. |
| Soluble Starch | 20.0 g. |
| Corn meal | 1.0 g. |
| Soybean meal | 4.0 g. |
| Glucose | 5.0 g. |
| $KH_2PO_4$ | 0.3 g. |
| Lard oil | 2.5 g. |
| Distilled water | 1000 ml. |
| pH 6.7 | |
| Medium M | |
| Dextrose | 10.0 g |
| Asparagine | 1.0 g |
| $K_2HPO_4$ | 0.1 g |
| $MgSO_4.7H_2O$ | 0.5 g |
| Yeast Extract | 0.5 g |
| Oat Flour | 10.0 g |
| $CaCO_3$ | 3.0 g |
| Trace Element Mix | 10.0 ml |
| Distilled water | 1000 ml |
| Adjust pH to 7.2 | |
| Trace Element Mix I | |
| $FeSO_4.H_2O$ | 1000 mg |
| $MnSO_4.4H_2O$ | 1000 mg |
| $CuCl_2.2H_2O$ | 25 mg |
| $CaCl_2.2H_2O$ | 100 mg |
| $H_3BO_3$ | 56 mg |
| $(NH_4)_6MO_4O_{24}.6H_2O$ | 19 mg |
| $ZnSO_4.7H_2O$ | 200 mg |
| Distilled water | 1000 ml |
| Medium N | |
| Medium G | 1000 ml |
| Oat Flour | 10 g |
| pH 7.2 | |

The fermentation employing *Penicillium charlesii* MF 5123 can be conducted at temperatures ranging from about 20° C. to about 40° C. For optimum results, it is most convenient to conduct these fermentations at a temperature in the range of from about 20° C. to about 30° C. Temperatures of about 24°–26° C. are most preferred. The pH of the nutrient medium suitable for producing the instant compounds can vary from about 3.0 to 8.5 with a preferred range of from about 4.0 to 7.0.

Small scale fermentations are conveniently carried out by placing suitable quantities of nutrient medium in a flask employing known sterile techniques, inoculating the flask with either spores or vegetative cellular growth of *Penicillium charlesii* MF 5123 loosely stoppering the flask with cotton and permitting the fermentation to proceed at a constant room temperature of about 25° C. on a rotary shaker at from 0 to 300 rpm for about 2 to 21 days. For larger scale work, it is preferable to conduct the fermentation in suitable tanks provided with an agitator and a means of aerating the fermentation medium. The nutrient medium is made up in the tank and after sterilization is inoculated with a source of vegetative cellular growth of *Penicillium charlesii* MF 5123. The fermentation is allowed to continue for from 5 to 20 days while agitating and/or aerating the nutrient medium at a temperature in the range of from about 20° to 28° C. The degree of aeration is dependent upon several factors such as the size of the fermentor, agitation speed, and the like. Generally the larger scale fermentations are agitated at about 95 to 300 RPM and about 2 to 20 cubic feet per minute (CFM) of air.

The fermentation of *Penicillium charlesii* MF 5123 is also successfully carried out in a solid fermentation medium under static, that is, non-agitated, conditions. The solid phase aerobic fermentation utilizes the same sources of carbon, nitrogen and inorganic salts as are used for the above-described submerged aqueous fermentation with the primary differences in the constitution of the medium being the quantity of water present. The solid phase fermentations constitute from 30 to 80% by weight of water. Where in comparison with a submerged fermentation medium which may utilize from 10 to 100 g of solid ingredients per liter of medium (1 to 10% w/v), a solid phase medium will contain from 20 to 70% w/v of the solid ingredients.

The solid phase fermentation may be carried out aerobically by maintaining a large ratio of surface area to the mass of the medium. This is readily accomplished by utilizing a 0.3 to 8 cm depth of medium in a fermentation tray or flask. Since the medium is not mechanically agitated, this ensures the presence of sufficient oxygen for growth. Alternatively the solid phase fermentation may be carried out in special trays fitted with sterile gauze for passing air through the solid medium or across the top thereof. Optionally the solid phase fermentation may be carried out with a tight fitting cover.

The fermentation of large scale portions of media may be carried out in stages of increasing quantities of media and it is not necessary that all of the stages be of the same type, that is aqueous or solid. It has been found to be preferable to carry out the initial stages of fermentation in aqueous media and transfer the media to larger scale solid media.

The compound of this invention is found primarily in the mycelium on termination of the *Penicillium Charlesii* MF 5123 fermentation and may be removed and separated therefrom as described below.

The separation of the Paraherquamide from the whole fermentation broth and the recovery of said compound is carried out by solvent extraction and application of chromatographic fractionations with various chromatographic techniques and solvent systems.

The instant compound has slight solubility in water, but is soluble in organic solvents. This property may be conveniently employed to recover the compound from the fermentation broth. Thus, in one recovery method, the whole fermentation broth is combined with approximately an equal volume of an organic solvent. While any organic solvent may be employed, it is preferable to use a water immiscible solvent such as ethyl acetate, methylene chloride, chloroform and the like. Generally several extractions are desirable to achieve maximum recovery. The solvent removes the instant compound as well as other substances lacking the antiparasitic activity of the instant compound. If the solvent is a water immiscible one, the layers are separated and the organic solvent is evaporated under reduced pressure. The residue is placed onto a chromatography column containing preferably, silica gel. The column retains the desired products and some impurities, but lets many of the impurities, particularly the non-polar impurities, pass through. The column is washed with a moderately polar organic solvent such as methylene chloride or chloroform to further remove impurities, and is then washed with a mixture of methylene chloride or chloroform and an organic solvent of which acetone, methanol, and ethanol and the like are preferred. The solvent is evaporated and the residue further chromatographed using column chromatography, thin layer chromatography, preparative layer chromatography, high pressure liquid chromatography and the like, with silica gel, aluminum oxide, ion exchange resins, dextrans gels and the like, as the chromatographic medium, with various solvents and combinations of solvents as the eluent. Thin layer, high pressure, liquid and preparative layer chromatography may be employed to detect the presence of, and to isolate paraherquamide. The use of the foregoing techniques as well as others known to those skilled in the art, will afford purified compositions containing the instant compound.

The instant compounds are potent endo-and ecto-antiparasitic agents against parasites particularly helminths, ectoparasites, insects, and acarides, infecting man, animals and plants.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunuculus and extra intestinal stages of the intestinal worms Strongyloides and Trichinella. The compouds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as aphids, (Acyrthiosiphon sp.); against migratory orthopterans such as locusts and immature stages of insects living on plant tissue. The compounds are useful as a nematocide for the control of soil nematodes and plant parasites such as Meloidogyne sp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the instant compounds in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents, and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of this invention may be administered to animals parenterally, for example, by intraruminal, intramuscular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active compounds are intimately dispersed throughout the carrier by methods such as grinding, stirring, milling or tumbling. Compositions containing from about 0.005 to 2.0% weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular compound employed, the compounds of this invention are usually fed at concentrations of between 0.00001 to 0.002% in the feed in order to achieve the desired antiparasitic result.

13

In using the compounds of this invention, the individual compounds may be prepared and used in that form. Alternatively, mixtures of the individual compounds may be used, or other active compounds not related to the compounds of this invention.

The compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

EXAMPLE 1

Seed cultures were prepared in medium 1 (20 ml in a 250 ml 3-baffle Erlenmeyer flask). The seed flasks were inoculated with spores of C. blakeleeana ATCC 8688a, 20926, MF-4415, and incubated on a rotary shaker (220 rpm) at 27° C. for 24 hours. The transformation flasks (40 ml medium 3 in 250 ml 3-baffle Erlenmeyer flask) were inoculated with 2 ml of seed culture and incubated at 27° C. on a rotary shaker. Methanol was used to solubilize paraherquamide for addition. The addition was made at 0 hour. The cultures were incubated for 2 days in the presence of 0.05 mg/ml paraherquamide. Following incubation, the whole broth was extracted as described in Example 2.

| Media: | g/L |
| --- | --- |
| Seed Medium 1 | |
| Dextrose | 4.0 g |
| Nutrient broth | 4.0 g |
| Yeast extract | 4.0 g |
| Malt extract | 10.0 g |
| 1000 ml distilled H2O pH | 7.3 |
| Slant Medium 2 | |
| Medium A plus agar | 20.0 g/L |
| Transformation Medium 3 | |
| Same as Medium 1 | |

EXAMPLE 2

The whole broth (200 ml) from Example 1 was adjusted to pH 7.5 with dilute sodium hydroxide, then centrifuged and filtered through filter paper to remove the mycelial cake. The fileted broth was extracted three times with ethyl acetate (3×200 ml). Ethyl acetate extracts were combined, dried over sodium sulfate, and concentrated under vaccum to an oily residue. The residue was chromtographed on preparative TLC (Merck Silica gel 60 PF$_{254}$) employing methylenechloride:methanol (90:10). The metabolites, located by UV lamp (254 nm), were scraped off, eluted with 50/50 methylenechloride:methanol and concentrated in vacuo. The residue was dissolved in acetonitrile and subjected to high performance liquid chromatography (HPLC) purification. HPLC was carried out on Whatman Partisil 10 ODS-3, 9.4 mm×25 cm column and monitored at 260 nm. The mobile phase consisted of an aqueous buffer (0.01M KH$_2$PO$_4$, 0.02M triethylamine, and pH adjusted to 7.0) and acetonitrile (65/35). Each compound was collected during repeated injections of the above described extract. The fractions of UV-absorbing material with similar HPLC retention times were pooled and evaporated to dryness in vacuo. Finally, each compound was dissolved in water and further purified using a C$_{18}$ Sep-Pak (Waters Associates) and methanol-water elution solvent to yield II (3 mg) with a retention time of 10.8 mintues, III (1 mg) with a retention time of 16.4 mintues, and IV (0.5 mg) with a retention time of 21.0 mintues wherein A is a double bond.

EXAMPLE 3

Following the procedures of the Examples 1 and 2 using dihydroparaherquamide in place of paraherquamide, there is obtained Compounds II, III and IV wherein A is a single bond.

PREPARATION 1

A 5% portion of an 18X150 MM test tube containing 3.5 g of soil and dried culture MF 5123 (ATCC 20841) was used to inoculate an unbaffled Erlenmeyer flask containing 50 ml of Medium 4. After three days of incubation of 28° C., agitated on a rotary shaker (5 cm throw) at 212 rpm, a 2.0 ml aliquot of the growth was aseptically transferred to a 250 ml Erlenmeyer flask containing Medium 5. After inoculation, Medium 5 was incubated 7 days without agitation at 25° C. After 7 days of incubation 15 ml of sterile distilled water was added to each flask. Incubation was then continued at 25° C. for a further seven days with agitation on a rotary shaker at 160 rpm.

PREPARATION 2

A 2.0 ml volume of a frozen vegetative growth in 10% glycerol of the culture MF 5123 (ATCC 20841) was used to inoculate an unbaffled Erlenmeyer flask containing 50 ml of Medium 4. After 3 days of incubation at 28° C., agitated on a rotary shaker (5 cm throw) at 212 rpm, a 2.0 ml portion of the growth was aseptically transferred to a 250 ml Erlenmeyer flask containing Medium 5. After inoculation, Medium 5 was incubated 7 days without agitation at 25° C. After 7 days of incubation 15 ml of sterile distilled water was added to each flask. Incubation was then continued at 25° C. for a further 9 days with agitation on a rotary shaker at 160 rpm.

PREPARATION 3

A 2.0 ml volume of a frozen vegetative growth in 10% glycerol of the culture MF 5123 (ATCC 20841) was used to inoculate an unbaffled Erlenmeyer flask containing 50 ml of Medium 4. After 3 days of incubation at 28° C., agitated on a rotary shaker (5 cm throw) at 212 rpm, a 2.0 ml portion of the growth was aseptically transferred to a 250 ml Erlenmeyer flask containing Medium 5. After inoculation, Medium 5 was incubated for 7 days without agitation at 25° C.

| Medium 4 | |
| --- | --- |
| Corn Steep Liquor | 5.0 g |
| Tomato Paste | 40.0 g |
| Oat Flour | 10.0 g |
| Glucose | 10.0 g |
| Trace Elements Mix | 10.0 ml |
| Distilled Water q.s. | 1000 ml |
| pH 6.8 | |
| Trace Elements Mix II | |
| FeSO$_4$.7H$_2$O | 1.0 g |
| MnSO$_4$.4H$_2$O | 1.0 g |
| CuCl$_2$.2H$_2$O | 25.0 mg |
| CaCl$_2$ | 0.1 g |
| (NH$_4$)$_6$MoO$_2$.4H$_2$O | 19.0 mg |

| -continued | |
| --- | --- |
| ZnSO$_4$.7H$_2$O | 0.2 g |
| Distilled Water q.s. | 1000 ml |
| Medium 5 | |
| Amount per 250 ml Erlenmeyer flask | |
| Corn | 10.0 g |
| Yeast extract | 0.5 g |
| Sodium tartrate | 0.1 g |
| FeSO$_4$.7H$_2$O | 0.01 g |
| L-cysteine | 0.1 g |
| Glycerol | 0.5 ml |
| CoCl$_2$.6H$_2$O | 0.002 g |
| Distilled Water | 15.0 ml |
| Autoclave | 20 minutes, 15 pounds, 121° C. |
| then Distilled Water | 10.0 ml |
| re-autoclave | 20 minutes, 15 pounds, 121° C. |

PREPARATION 4

The contents of six seven day solid media 250 ML fermentation flasks from Preparation 3 were combined and extracted twice with six hundred ml. of ethyl acetate. The extracts were combined, dried with sodium sulfate and concentrated to 60 ml.

A three ml. aliquot of the 60 ml concentrate was further concentrated to 0.5 ml. This sample was subjected to preparative thin layer chromatography on an E. Merck Silica-Gel 60 (0.5 mm thickness) plate using a solvent system of 5:5:0.5 v/v/v hexane:methylene chloride:methanol. After chromatography nine zones were selected by U.V. quenching and iodine staining of a template section of the plate. The selected areas were scraped and each eluted with 2 ml. of methanol. The eluted samples were labeled A thru I. One hundred mcl of each sample was submitted for *C. elegans* assay. Sample C Rf=0.16 was active against *C. elegans*. Sample C was concentrated to dryness and the residue taken up in 400 mcl of methanol and subjected to preparative HPLC chromatography on a DuPont Zorbax ODS 0.94×25 cm column maintained at 60 degrees C. The chromatography was carried out using an isocratic system of 65:35 v/v methanol:water at a flow rate of 4 ml/min. for thirty minutes followed by a linear gradient to 100% methanol over 10 minutes and held at 100% methanol for 35 minutes. The effluent stream was monitored at 226 nm and a setting of 1.28 AUFS using a Laboratory Data Control SpectroMonitor II detector equipped with a 1 mm path length cell, and a Spectra-Physics SP4100 Computing Integrator. Twenty five fractions were collected. Fraction nine with a retention time of 11.3 minutes was active against *C. elegans*. Fractions eight thru twelve were combined and concentrated to dryness. The residue was labeled J and submitted for N.M.R. and mass spectral analysis and identified as structure I Paraherquamide. Sample J contained 1.8 mg. of paraherquamide based on U.V. analysis using published U.V. data (*Tetrahedron Letters* Vol. 22 pp 135–136 1980).

PREPARATION 5

The contents of sixteen-seven day solid media 250 ml fermentation flasks from Preparation 3 were combined and extracted with three one liter portions of ethyl acetate. High pressure liquid chromatography (HPLC) analysis of the three extracts indicated that extracts one and two contained 430 and 130 mg respectively of paraherquamide. Extract three contained only 4 mg and was discarded. Extracts one and two were combined and dried with sdium sulfate. The dried extract was concentrated to an oily residue. The residue was taken up in methanol to a volume of 40 ml. This solution was chromatographed on a 200 ml column of LH-20, previously equilibrated with methanol, using methanol at a flow rate of 3 ml./min collecting a 40 ml fore cut followed by sixty-one seven ml fractions. HPLC analysis showed that fractions 10 thru 16 contained paraherquamide Rt=7.9 minutes. Fractions 10 thru 16 were combined and concentrated to an oily residue. The residue was taken up in 5:5:0.5 v/v/v hexane:methylene chloride:methanol to a volume of 13.5 ml. This solution was chromatographed on a 500 ml column of E. Merck Silica-Gel 60 (0.04 to 0.063 mm particle size) previously equilibrated with the same solvent system at a flow rate of 10 ml/min. A 200 ml forecut was collected followed by 315 eight ml fractions. Fractions were combined as follows based on T.L.C. analysis. Fractions 150 to 179; 180 to 199; 200 to 239; 240 to 270; and 271 to 315. The combined fractions were labeled A thru E. Samples C and D were combined, concentrated to dryness and labeled F. Sample F was taken up in 2 ml of methanol and filtered. The filtrate was subjected to preparative HPLC chromatography using a Whatman Magnum 20 ODS-3 2.2×25 cm column at room temperature using an isocratic solvent system of 68/32 v/v methanol/water at a flow of 10 ml/min. The effluent stream was monitored using a Gilson model 116 U.V. detector equipped with a 0.05 mm path length cell and a setting of 1.28 AUFS, the detector signal being monitored by a Spectra-Physics SP4100 Computing Integrator. Thirty fractions were collected. Fractions 16 thru 18 were combined, based on the U.V. recording. The combined fractions were concentrated to dryness to yield 205.4 mg of pure paraherquamide, structure I.

PREPARATION 6

Solid Phase Fermentation. The inoculant was prepared by placing the contents of one frozen vial of MF-5123 (ATCC 20841) into 54 ml of medium 4 in a 250 ml flask and agitated at 28° C. for 48 hours on a rotary shaker at 220 rpm. At the completion of the fermentation period 10 of the fermentation broth was transferred to 800 ml of medium 4 in a 2 liter flask and agitated at 28° C. for 48 hours on a rotary shaker at 200 rpm.

The production medium was prepared by dissolving all of the ingredients of medium 6 except the cracked corn in 3.5 l of distilled water and combining this solution with 3 kg of cracked corn in a 50×75×5 cm filter tray. The tray was sterilized uncovered for 20 minutes at 121° C. The contents of the tray were stirred and another tray of the same dimension was placed over the first as a lid and taped tightly closed. The covered tray was autoclaved for an additional 20 minutes at 121° C. The tray was removed from the autoclave and allowed to cool for several hours before inoculation. After cooling, the tray was inoculated with 1 liter of the inoculant. The inoculant was distributed uniformly throughout the medium by mixing with a sterile spatula. The lid was taped securely to the tray and the solid culture fermented at 25° C. for several days without agitation.

The above solid phase fermentation was repeated using the same procedure with the exception that after the uncovered sterilization 2.0 liter of distilled water was added to the tray.

| Medium 6 (Solid phase production medium) | |
| --- | --- |
| Material | concentration (g/tray) |
| Cracked corn (Agway) | 3000.0 |
| Yeast extract | 150.0 |
| Sodium tartrate | 30.0 |
| $FeSO_4 \cdot 7H_2O$ | 3.0 |
| $CoCl_2 \cdot 6H_2O$ | 0.6 |
| L-cysteine | 30.0 |
| Glycerol | 150.0 |
| pH - No adjustment | |

PREPARATION 7

A tray of 3 kg of solid media from Preparation 6 and 20 flasks containing 80 gm of solid media (2) each from Preparation 3 were extracted with ethyl acetate using 2×600 ml of solvent per flask and 2×4 liters of solvent per tray. The extracts were combined, labeled A and stored at 5° C. A tray of 3 kg solid media (5) and 20 flasks containing 80 gm of solid media per flask were extracted with ethyl acetate and the extracts combined and labeled B.

Samples A and B were combined and concentrated, under reduced pressure at 26° C., to 800 ml. This concentrate was further concentrated, using high vacuum and a 40° C. water bath, to a volume of 300 ml. Three hundred ml of methanol was added to the oily concentrate. Precipitation was observed and the solution was stored at 5° C. overnight. The precipitate was removed by filtration and washed with 200 ml of methanol. The filtrate and the methanol wash were combined giving a volume of 800 ml which was labeled C. HPLC analysis of Sample C indicated the presence of 4.3 gm of paraherquamide. Sample C was concentrated under reduced pressure, to remove methanol to a final volume of 200 ml. To this concentrate 200 ml of acetonitrile was added and labeled D. Solution D was extracted with 1×400 ml of hexane followed by 3×300 ml hexane extractions. The acetonitrile layer, 310 ml, contained 3.9 gm of paraherquamide, by HPLC analysis. The acetonitrile solution was concentrated to dryness and labeled E. The hexane extracts were discarded.

PREPARATION 8

Sample E from Preparation 7 was taken up in 1:1 methylene chloride/ethyl acetate to a volume of 180 ml. The solution was chromatographed on a 4 liter column of silica gel (Grace), which had previously been equilibrated with ethyl acetate. The chromatography was carried out with ethyl acetate at a flow rate of 200 ml/min collecting five four liter fractions followed by 24×500 ml fractions. Fractions 3 thru 9 containing 1.95 gms of paraherquamide were combined and labeled F. Fraction two, which was highly colored and contained considerable paraherquamide, was concentrated to dryness for rechromatography. The residue, which was labeled G, was taken up in 1:1 methylene chloride:ethylacetate to a volume of 180 ml and chromatographed as above. Five four liter fractions followed by 24×500 ml fractions were collected. Fractions 4 thru 17 containing paraherquamide were combined and labeled H. Samples F and H were combined. HPLC analysis of the combined fractions indicated they contained 4 gms of paraherquamide. The combined sample was concentrated to yield 9.5 grams of solids which were labeled J.

PREPARATION 9

Sample J from Preparation 8 was taken up in 3:1 methanol:methylene chloride to a volume of 110 ml and applied to a 2"×6' Sephadex LH 20 column previously equilibrated with methanol. Chromatography was carried out with methanol at a flow rate of 20 ml/min collecting 20 ml fractions. The fractions were analyzed by T. L. C. and HPLC and paraherquamide was found to be present in fractions 155 thru 186. Fractions 155 thru 164 combined and labeled A. Fractions 165 thru 175 combined and labeled B. Fractions 176 thru 186 combined and labeled C. Samples A and B were each concentrated to dryness and their residue triturated with 20 ml of cold ethyl acetate. The triturates were filtered and the solids combined and labeled D. The filtrates were combined and labeled E.

PREPARATION 10

Sample D from Preparation 9 was taken up in 80 ml of 2:1 hexane:acetone and chromatographed, in two 40 ml portions, on silica gel (Grace) previously equilibrated with 2:1 hexane acetone. Portion one was chromatographed on one liter of silica gel and portion two on 700 ml of silica gel. Chromatography in both instances was carried out with 2:1 hexane:acetone at a flow rate of 20 ml/min collecting 25 ml fractions. Fractions 153 thru 220 and 143 thru 230 from the respective columns contained a total of 3.5 gms of paraherquamide.

PREPARATION 11

Paraherquamide (5 mg, 0.01 moles) was dissolved in 2 mL of methanol. 10% palladium-on-carbon (5 mg) was added and hydrogenation carried out under 40 psig, 23° C. for 2.5 hours. Reaction was 100% completed after 2.5 hours and no side products were observed as determined by HPLC and TLC. The reaction mixture was filtered and the catalyst washed with methanol. The combined methanol solutions containing dihydroparaherquamide were taken to dryness and purified initially by HPLC on an analytical Whatman ODS-3 column using a 60:40, water:methanol 1% acetic acid and 0.1% triethylamine solvent system delivered at 1.5 mL/min. A 40% aqueous methanol solvent system was used subsequently for final purification. Identification was based on mass spectral and NMR analyses.

What is claimed is:

1. Compounds having the formulae:

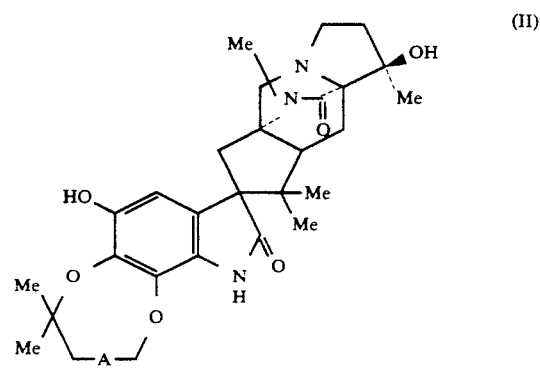

(II)

-continued

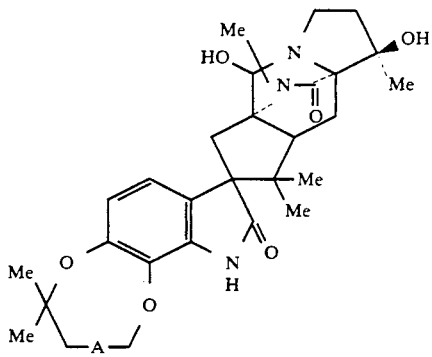
(III)

wherein A is a single or a double bond.

2. The compound of claim 1 wherein A is single bond.

3. The compound of claim 1 wherein A is a double bond.

4. The compound of claim 3 which is Compound II.

5. The compound of claim 3 which is Compound III.

6. A method for the treatment of parasitic infections in animals which comprises administering to animals infected with parasites an effective amount of a compound of claim 1.

7. A composition useful for the treatment of parasitic infections in animals which comprises an inert carrier and an effective amount of a compound of claim 1.

* * * * *